US005893397A

United States Patent [19]

Peterson et al.

[11] Patent Number: 5,893,397

[45] Date of Patent: Apr. 13, 1999

[54] MEDICATION VIAL/SYRINGE LIQUID-TRANSFER APPARATUS

[75] Inventors: Steven F. Peterson, West Linn; Michael F. Deily, Tigard, both of Oreg.

[73] Assignee: Bioject Inc., Portland, Oreg.

[21] Appl. No.: 08/586,566

[22] Filed: Jan. 12, 1996

[51] Int. Cl.$^{6}$ ..................................................... A61M 5/30

[52] U.S. Cl. ........................... 141/27; 141/329; 141/378; 141/383; 141/386; 604/411; 604/414

[58] Field of Search ........................... 141/18, 21, 25–27, 141/329, 330, 383, 385, 386, 378; 604/403, 411, 414

[56] References Cited

U.S. PATENT DOCUMENTS

| | | |
|---|---|---|
| D. 268,698 | 4/1983 | Knute . |
| D. 297,262 | 8/1988 | Sternweiler . |
| D. 349,958 | 8/1994 | Hollis et al. . |
| 2,584,397 | 2/1952 | Pitman . |
| 3,580,423 | 5/1971 | Gilman ..................................... 222/81 |
| 3,729,031 | 4/1973 | Baldwin ................................ 141/27 X |
| 3,779,371 | 12/1973 | Rovinski . |
| 3,938,520 | 2/1976 | Scislowicz et al. . |
| 3,940,003 | 2/1976 | Larson ..................................... 215/247 |
| 4,128,098 | 12/1978 | Bloom et al. . |
| 4,505,709 | 3/1985 | Froning et al. ......................... 604/411 |
| 4,507,113 | 3/1985 | Dunlap ...................................... 604/71 |
| 4,515,586 | 5/1985 | Mendenhall et al. . |
| 4,516,967 | 5/1985 | Kopfer ...................................... 604/87 |
| 4,543,101 | 9/1985 | Crouch . |
| 4,564,054 | 1/1986 | Gustavsson ............................ 141/329 |
| 4,568,346 | 2/1986 | van Dijk ................................. 604/414 |
| 4,581,014 | 4/1986 | Millerd et al. ........................... 604/80 |
| 4,607,671 | 8/1986 | Aalto et al. ............................ 141/329 |
| 4,614,437 | 9/1986 | Buehler .............................. 141/329 X |
| 4,636,204 | 1/1987 | Christopherson et al. ............. 604/283 |
| 4,662,878 | 5/1987 | Lindmayer . |
| 4,675,020 | 6/1987 | McPhee .................................. 604/411 |
| 4,759,756 | 7/1988 | Forman et al. ......................... 604/413 |
| 4,834,149 | 5/1989 | Fournier et al. ........................... 141/1 |
| 4,872,494 | 10/1989 | Coccia .................................... 141/383 |
| 4,883,483 | 11/1989 | Lindmayer . |

(List continued on next page.)

FOREIGN PATENT DOCUMENTS

| | | | |
|---|---|---|---|
| 681331 | 9/1939 | Germany | ............................. 141/378 |

*Primary Examiner*—J. Casimer Jacyna
*Attorney, Agent, or Firm*—Kolisch Hartwell Dickinson McCormack & Heuser

[57] ABSTRACT

Liquid-transfer apparatus, and methodology employing the same, operatively interposable a syringe and a vial, and accommodating both a single-mouth-size (single-size), two-vial transfer procedure, and a two-mouth-size (two-size), two-vial transfer procedure. The apparatus includes a liquid-transfer device having a syringe-coupling end, a vial-coupling end, and liquid-passage structure effectively communicating between these ends. In the case of accommodating a single-mouth-size (single-size), two-vial procedure, only the liquid-transfer device is employed, and the same is sized with a vial-coupling end that is constructed for direct coupling to the top of the single-size vial which is used. In the case of accommodating a two-mouth-size (two-size), two-vial operation, the liquid-transfer device is employed along with a vial-coupling adaptor which is removably receivable in a connected relationship with the vial-coupling end in the device to adapt the same for coupling to the top of a vial having the smaller of the two sizes of vials which are to be employed. Under these circumstances, the entire procedure begins with coupling of the apparatus to a syringe and to the smaller-size vial, with the vial-coupling adaptor connected to the liquid-transfer device's vial-coupling end. Following a liquid-transfer operation with this smaller vial, the same is decoupled, and such decoupling automatically disconnects the vial-coupling adaptor and the liquid-transfer device. Thereafter, a vial of the larger size is coupled to the vial-coupling end in the liquid-transfer device, and a transfer procedure is completed between the syringe and the larger coupled vial.

10 Claims, 3 Drawing Sheets

U.S. PATENT DOCUMENTS 4,886,495 12/1989 Reynolds .
4,913,699 4/1990 Parsons .
4,936,841 6/1990 Aoki et al. .............................. 604/413
4,940,460 7/1990 Casey et al. .
4,941,880 7/1990 Burns .
4,944,736 7/1990 Holtz ........................................ 604/403
4,966,581 10/1990 Landau .
4,997,430 3/1991 Van der Heiden et al. .
5,088,996 2/1992 Kopfer et al. ...................... 141/329 X
5,100,394 3/1992 Dudar et al. ............................ 604/283
5,163,583 11/1992 Whitworth .................................. 222/1
5,195,992 3/1993 Dudar et al. .
5,211,638 5/1993 Dudar et al. ............................ 604/283
5,279,576 1/1994 Loo et al. .............................. 604/187
5,281,198 1/1994 Haber et al. .
5,304,165 4/1994 Haber et al. ............................ 604/411
5,312,335 5/1994 McKinnon et al. .
5,312,577 5/1994 Peterson et al. .
5,334,179 8/1994 Poli et al. .............................. 604/403
5,364,386 11/1994 Fukuoaka et al. .
5,383,851 1/1995 McKinnon, Jr. et al. .
5,399,163 3/1995 Peterson et al. .
5,466,220 11/1995 Brenneman .............................. 604/87
5,472,022 12/1995 Michel et al. ...................... 141/383 X
5,503,627 4/1996 McKinnon et al. .
5,505,697 4/1996 McKinnon, Jr. et al. .
5,526,853 6/1996 McPhee et al. ........................ 141/329
5,647,845 7/1997 Haber et al. ............................ 604/411

20
22
22a
22b
22c
24
24a
24b
24c
24d
24e
24f
24g
24h
24i
26
26a
26b
26c
28
30
32
34
34a
36
36a
36b
38
38a
40
40a
42
42a
42b
44
44a
2A
L
W 22
22a
22b
22c
22d
24
26
26b
30
38
38a

MEDICATION VIAL/SYRINGE LIQUID-TRANSFER APPARATUS

TECHNICAL FIELD

The present invention relates to liquid-transfer apparatus which is interposable a syringe and a medication vial for facilitating the passage of liquid therebetween during the preparation of a dispensible pharmaceutical.

BACKGROUND AND SUMMARY OF THE INVENTION

In the field of medicine, it is often the case that liquid pharmaceuticals must be prepared for delivery to a patient by a syringe. Such preparation typically involves the withdrawing into a syringe of a diluent liquid contained in a first vial, the subsequent injection of that liquid from the syringe into a second vial which contains a blendable, dissolvable medicine in powder form, and thereafter the withdrawal of the now-blended pharmaceutical medicine from that second vial back into the syringe. It is most frequently, though not always, the situation that the first vial from which diluent liquid is withdrawn is smaller (in mouth-opening-diameter size) than the second vial wherein blending occurs—which second vial has a larger mouth-opening-diameter size. A procedure falling within this category is referred to herein as involving first a smaller-size vial, and thereafter a larger-size vial. One should note that such references to smaller, and larger vial sizes are related to mouth-opening sizes, and not necessarily to vial volume sizes. In the balance of preparation situations, two vials of the same mouth-opening size are employed throughout the operation.

To aid in the practice of such back-and-forth transfer/delivery of liquid between a vial and a syringe, and to take into account safety and health concerns regarding, inter alia, contaminization, loss of sterilization, and exposure of medical personnel to injuries from sharps (such as hypodermic needles), prior work in this field has witnessed the creation and development of various liquid-transfer devices, or interfaces, which allow both for convenient coupling to a syringe and to a vial for liquid transfer, and for minimization of the several kinds of safety and health concerns just mentioned.

Two issues which are not well addressed by known prior art approaches to such liquid-transfer requirements are, first, that highly convenient accommodation of transfer apparatus to the handling of two different vial sizes has not been offered, and second, that a testy problem, referred to as "foaming", has not apparently been well addressed. Foaming is a bubbling action which can and does readily occur during that part of a liquid-transfer process wherein diluent is injected into a vial containing dissolvable powdered medicine. Foaming introduces problematic air bubbles which must be removed before any delivery to a patient.

An important object of the present invention, accordingly, is to provide an improved form of liquid-transfer apparatus which offers all of the key advantages of known prior art devices aimed at this purpose, but which, in addition, avoids the drawbacks (i.e., the not well-addressed issues) mentioned above.

More specifically, an object of this invention is to provide such apparatus which readily and easily accommodates transfers back and forth of liquid between a syringe and vials of the same size, as well as such transfers between a syringe and vials of two different sizes.

Another significant object of the invention is to provide transfer apparatus which uniquely creates an "ejection" liquid-flow into a vial that contains dissolvable powdered medicine in a fashion that greatly minimizes, and in very many instances completely avoids, the problem mentioned above known as foaming.

Still a further object of the present invention is to provide liquid-transfer apparatus of the type generally outlined which includes a ported spike which pierces and extends through the usual elastomeric stopper found in a vial, and which, further, is constructed in such a manner that with the spike piercing a conventional stopper, ports in the spike are contained within the usually present inwardly facing "cup" in the stopper, and in particular, in a condition closely adjacent the base in the cup. This offering of the invention plays not only a role in achieving the immediately preceding stated object of the invention, but in addition, ensures a situation wherein it is possible, predictably, and with no special effort required, and during withdrawing of liquid from a vial, to gather substantially all of the liquid in that vial.

Considering what we view to be the preferred organization of the present invention, that organization takes fundamentally two different forms. In one form, which form is designed to deal with the situation where only vials of the same size are ever used, the apparatus of the invention employs but a single unit, which we refer to as a liquid-transfer device. This device has a syringe-coupling end, a vial-coupling end which is sized to accommodate coupling to the particular single vial size that will be encountered, and special liquid passage structure which extends effectively for communication between the two mentioned ends of the device. The second organizational form of the invention is aimed at addressing, inter alia, the situation where two different sizes of vials need to be coupled-to during a preparation operation. In this form of the invention, two components are employed. One of these is a liquid-transfer device of the kind just mentioned above, with this transfer device being sized, at its vial-coupling end, to accommodate coupling to the larger size of the two vials which will be addressed. The other component takes the form of a slider/adaptor that fits in a connected (such as nested), removable relationship with respect to the vial-coupling end in the transfer device to accommodate direct coupling to a vial of the smaller of the two vial sizes which will be addressed.

With respect to both of these two forms of the invention, when an appropriate vial (of any size) is coupled-to for a liquid-transfer operation, and under circumstances where liquid is being injected through the transfer device into an attached vial, the liquid passage structure mentioned above directs liquid flow into the vial via a pair of tiny, laterally facing ports which reside, relatively positionally, within the hollow interior of an annular projection formed in the vial's stopper, which hollow interior faces the interior of the vial. This conventional annular projection and hollow interior thereof define what is referred to herein as a cup that faces (axially) the interior of the associated vial, and the port in the apparatus of the invention is located within the interior of this cup and closely adjacent the base of the cup. With this relationship extant—a relationship which exists because of certain special constructional features proposed according to the invention—and with the two ports organized as generally described, liquid flow into a vial is predominantly generally radial in nature, and uniquely suited to creating major liquid flow into the vial down the inside wall of the vial to minimize foaming.

Another feature of this kind of relationship which exists between the ports of the invention and the stopper's cup under circumstances where liquid is being withdrawn from a vial is that, with appropriate inversion of a vial, substantially all of liquid content can easily be withdrawn.

These and other objects, features and advantages which are offered by the present invention will become more fully apparent as the description that now follows is read in conjunction with the accompanying drawings.

Figures 1, 2, 2A, 3, 4, 5:
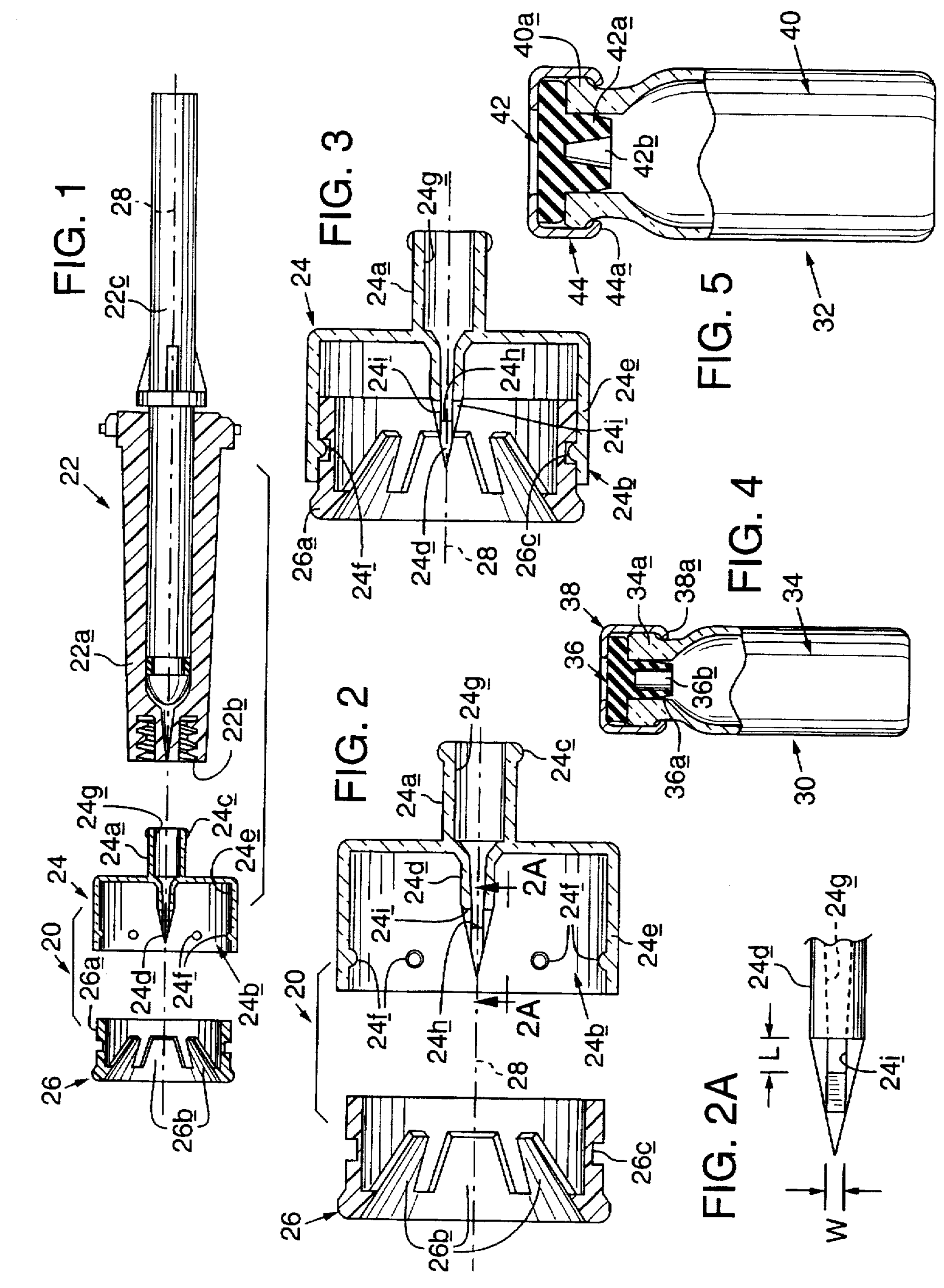
FIG. 1 is a side elevation of apparatus constructed in accordance with the present invention, displayed horizontally alongside a conventional syringe with respect to which it is intended for use. The apparatus of the invention (pictured in cross section in the figure) includes two elements (shown separated), both of which are employed according to one organization of the invention designed to handle two different sizes of vials, and one only of which is employed according to another organization of the invention wherein only a single-size vial is involved.
FIG. 2 is a view, on a larger scale than that employed in FIG. 1, of the two invention components pictured in FIG. 1.
FIG. 2A is an enlarged, fragmentary detail taken generally along line 2A—2A in FIG. 2.
FIG. 3 is a view on about the same scale as that used in FIG. 2, illustrating the two "separated" components of FIG. 2 assembled horizontally in such a fashion that the left-hand component in the figure is slidably nested within structure that forms part of the right-hand component in the figure.
FIG. 4 is a side view, partly in cross section, illustrating what is referred to herein as a smaller-size vial, with this vial displayed in a vertical or upright condition.
FIG. 5 is an upright side view, partly in cross section, of what is referred to herein as a larger-size vial.

Various features illustrated in the drawings, though close to, are not necessarily depicted in exact scale and/or proportion.

DETAILED DESCRIPTION OF, AND BEST MODE FOR CARRYING OUT, THE INVENTION

Turning attention now to the drawings, and referring first of all to FIGS. 1 and 2, indicated generally at 20, in non-attached, non-coupled condition, is liquid-transfer apparatus constructed in accordance with the present invention. This apparatus is intended for use, as will be explained, with a conventional syringe, such as the syringe shown in FIG. 1 at 22. Apparatus 20 includes what we refer to herein as a liquid-transfer device 24, and a vial-coupling adaptor 26. In the most commonly used form of the invention, both device 24 and adaptor 26 are employed. In a somewhat less common application, only device 24 is employed. Initially, the description of the invention herein will proceed with the view that both device 24 and adaptor 26 are used. Following that description will come a description of how the invention is employed utilizing only device 24.

Syringe 22 which, as has been mentioned, is a conventional syringe, includes a body 22a having a communication end 22b which is, in the specific style of syringe illustrated, threaded for a so-called (and well-known) Luer-type screw connection, and an elongate plunger 22c. While syringe 22 is described and illustrated herein in conjunction with having a Luer-type screw connection at its communication end, it could just as well be formed with what is known as a Luer-type tapered compression (non-screw) connection at that end, or, in fact, with any other type of appropriate connection.

Focussing attention now on the details of construction of the two invention components illustrated, transfer device 24, which preferably is formed of a suitable molded thermoplastic material, includes a syringe-coupling end 24a that joins unitarily with a vial-coupling end 24b. End 24a is constructed, as illustrated herein, with threading projection structure 24c which accommodates a screw connection with communication end 22b of syringe 22. It should be understood, of course, that end 24a can be constructed accordingly to accommodate connection with syringes having various other styles of communication ends. Device 24 is, in large part, a body of revolution which is centered on and about a longitudinal axis shown at 28.

End 24b is formed with a central vial-stopper-piercing spike 24d which is symmetrically circumsurrounded by an annular shroud/collar 24e, on the inside cylindrical wall of which are formed plural, distributed, slightly domed protuberances, such as protuberance 24f. These protuberances, of which there are six, equiangularly distributed, are disposed close to the left open face of end 24b in FIGS. 1 and 2. As will be explained later, they function as a vial-grip structure.

Extending axially centrally into end 24a, and partially into end 24b via spike 24d, is what can be thought of as, generally, a stepped-diameter central channel 24g. The right end of channel 24g in FIGS. 1 and 2 is open along axis 28, whereas the left end of this channel in these figures is barriered across axis 28 by a generally planar barrier wall 24h. Wall 24h extends in a plane which is substantially normal to axis 28.

Considering now FIG. 2A along with FIGS. 1 and 2, communicating with the left end of channel 24g in FIGS. 1 and 2 are two, generally rectangular, laterally-facing ports 24i. Focusing attention especially on FIG. 2A, each of ports 24i has a width, measured as indicated by the letter W, lying within the range of about 0.02- to about 0.03-inches, and preferably toward the lower end of this range. The length of each port, indicated by L, preferably lies within the range of about 0.02- to about 0.03-inches. Dimensions W and L, referred to herein as transverse dimensions, and as seen in FIG. 2A, mark the lateral boundaries of what is referred to herein as an exit profile for the port which has an area lying within the range of about $0.0004\text{-in}^2$ to about $0.0009\text{-in}^2$, and preferably with an area toward the lower end of this range. In the particular embodiment now being described dimension W is slightly smaller than dimension L. Barrier wall 24h is referred to herein as at least partially defining a region of communication between channel 24g and ports 24i. The channel and ports are referred to collectively herein as a liquid-passage structure.

In relation to the delivery of liquid through device 24 from end 24a toward end 24b, end 24a is referred to as the upstream end of the device, and end 24b as the downstream end. Such liquid delivery results in ejection of liquid from ports 24i which is limited predominantly to generally radial flow relative to long axis 28.

Continuing a description of device 24, and in the context of the apparatus of the invention being used in conjunction with two different sizes of vials, the inside of shroud/collar 24e is sized to receive, directly and moderately snugly, the banded mouth end (top) of the larger one of the two vial sizes involved. In particular, it is adapted to receive this vial end in such a fashion that what we refer to as the underside shoulder of the band in the vial is borne against, and gripped in place, by protuberances 24f. This condition is clearly illustrated in, and will be mentioned again in conjunction with, another drawing figure still to be discussed. A special feature to note at this point is that, effectively, protuberances 24f are located downstream from ports 24i relative to channel 24g. It is this relationship which results in important positioning of ports 24i within the cup of the typical vial stopper—a condition also still to be described in relation with a yet-to-be-discussed, other drawing figure.

Adaptor 26 is preferably formed of a suitable molded thermoplastic material. It includes an outer cylindrical skirt portion, or skirt, 26a, extending inwardly from the left end of which in FIGS. 1 and 2 are plural, conically converging spring fingers, such as those shown at 26b. Extending circumferentially around the outside of skirt 26a at an appropriate location axially therealong, which location will be discussed more fully shortly, is a shallow groove 26c. The left side or end of adaptor 26 in FIGS. 1 and 2 is referred to herein as its vial-facing end.

Considering FIG. 3, now along with FIGS. 1 and 2, adaptor 26 is intended to coact with transfer device 24 to adapt the same for dealing with the smaller-size vial that is employed in a two-size, two-vial preparation operation. At the beginning of such an operation, adaptor 26 is inserted slidably into shroud/collar 24e to the received position indicated in FIG. 3. In this received position, protuberances 24f snap, in a detent-like way, into groove 26c, thus to tend to retain device 24 and adaptor 26 in a fit-together connected condition. The particular connected condition, or relationship, illustrated in FIG. 3 is one that we refer to as a "nested" condition. Other fit-together, connected conditions could, of course, be used.

During operation of the apparatus of the invention with the mentioned smaller-size vial, when the top of that vial is coupled to the apparatus, the underside shoulder of the band surrounding the mouth in that vial is borne against, and gripped by, the inner free ends of fingers 26b in adaptor 26. These fingers, therefore, are referred to also herein as vial-grip structure. Looking especially at what is illustrated in FIG. 3, in the embodiment of the invention now being described, with device 24 and adaptor 26 in the relative positions indicated in FIG. 3, one can see that the free ends of the fingers are located "downstream" from ports 24i.

FIG. 4 illustrates at 30 what is referred to herein as a smaller-size vial, and FIG. 5 illustrates at 32 what is referred to herein as a larger-size vial. The most commonly used vial sizes today in the field of medicine are referred to as 13-mm vials and 20-mm vials, and accordingly, the apparatus of the invention now being described is specifically sized to handle these two sizes of vials. These two discussions are vial mouth diameter dimensions. It should be evident to those skilled in the art that the apparatus could be sized to handle other specific vial sizes if so desired.

Vial 30 includes a vessel 34 with a mouth 34a which is closed off by an elastomeric stopper 36 that is held in sealing relationship with mouth 34a by an annular band, typically a metallic band, 38 which has what we refer to herein as an underside shoulder 38a. The upper central surface of stopper 36 is exposed for piercing to gain access to the interior of the vessel, and the underside of this stopper, as pictured in FIG. 4, includes a hollow-interior, central, annular projecting wall structure 36a which has an open end (the lower end in FIG. 4) facing, axially, the interior of vessel 34. This open end defines in stopper 36 a cup 36b that has a downwardly facing base 36c. In a two-size, two-vial procedure, the smaller-size vial, like vial 30, contains an appropriate liquid diluent.

With the exception of the fact that vial 32 is larger than vial 34, vial 32 is, generically in other respects, substantially the same as vial 30. Thus, vial 32 includes a vessel 40 with a mouth 40a which is closed by an elastomeric stopper 42 that is held in sealing relationship with the vessel by an annular band 44 which has an underside shoulder 44a. Stopper 42 includes a wall structure 42a which is somewhat like previously-mentioned wall structure 36a, and a cup 42b which is somewhat like previously-mentioned cup 36b. Cup 42b has a downwardly facing base 42c.

In a two-size, two-vial procedure, the larger-size vial, like vial 32, contains, at least initially, powdered medicine which is dissolvable in and by the diluent contained in the smaller-size vial.

Having thus now described the constituent elements of the apparatus of the present invention, and the external structures (syringe and vials) with respect to which the invention is intended for use, let us now launch into a typical two-size, two-vial liquid pharmaceutical preparation procedure.

As was mentioned earlier, FIG. 6 in the drawings illustrates the beginning of the procedure wherein device 24 and adaptor 26 are fit together, and the communication end of syringe 22 is coupled to syringe-coupling end 24a in device 24.

Figures 6, 7, 8, 9, 10:
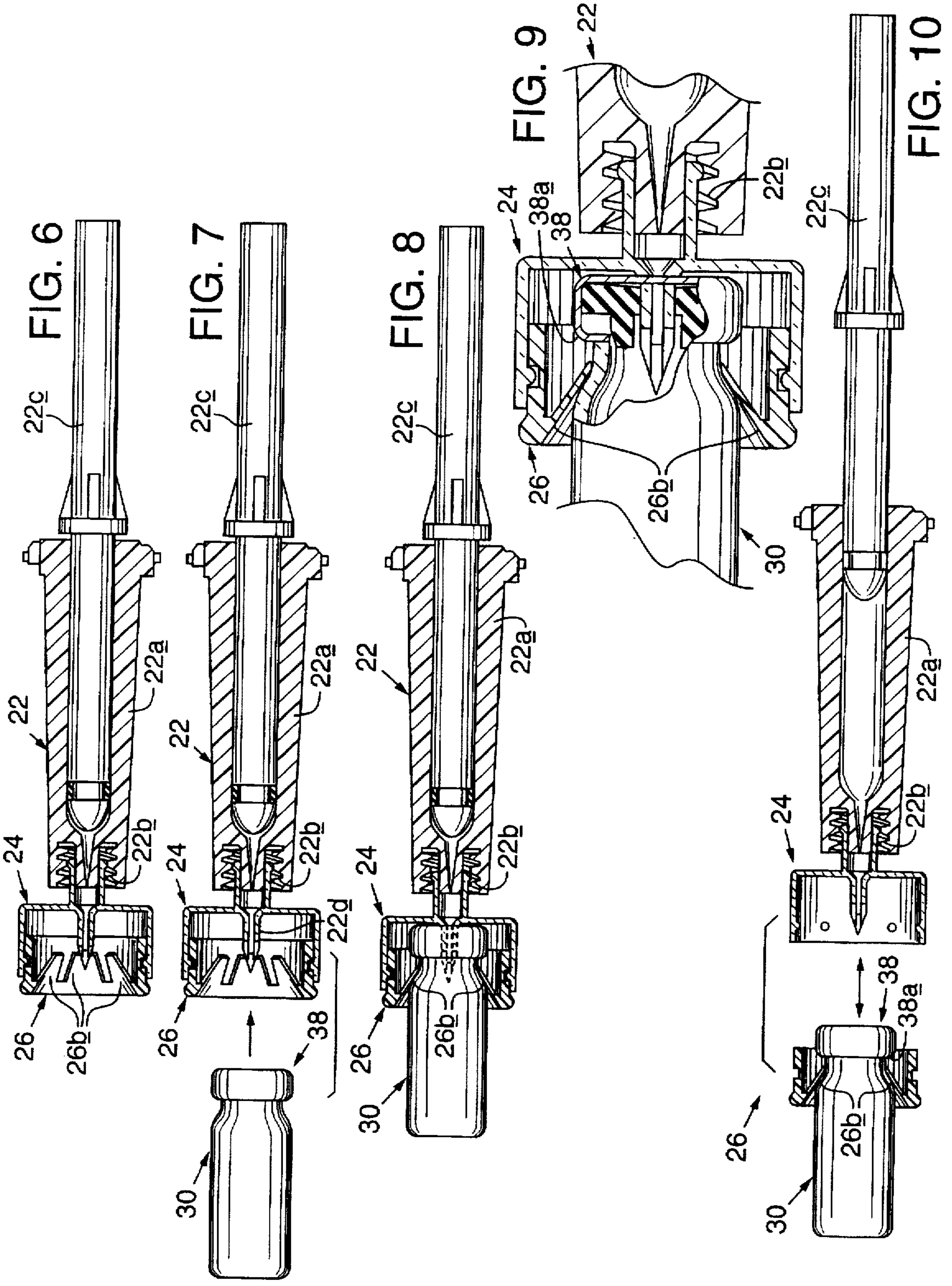
FIG. 6 shows the apparatus and syringe of FIG. 1 in fully-assembled form in a condition of readiness to begin a pharmaceutical preparation operation involving the sequential coupling to two different vial sizes, beginning with coupling to a smaller vial size, and ending with coupling to a larger vial size, as will shortly be explained.
FIGS. 7–14, inclusive, illustrate stages in the use of the apparatus of this invention to perform a liquid pharmaceutical preparation of the most commonly encountered type which requires sequential coupling to two different sizes of vials, commencing with the smaller one of these two sizes.

This assemblage is then confronted with the mouth end of a diluent-containing, smaller-size vial, like vial 30, and as pictured in FIG. 7, these two separated elements are driven toward one another until the vial is fully coupled to the transfer apparatus—a condition illustrated in FIG. 8. The conical organization of fingers 26b tends to guide and direct the vial centrally into vial-coupling end 24b, and into a condition with spike 24d centrally piercing the stopper in the vial. The inner ends of fingers 26b bear against the underside shoulder of the band in the vial, and tend to hold the vial in place against involuntary ejection under the now-present influence of the deflected central portion of the vial's stopper.

Focusing attention on FIG. 9 which, as has been mentioned, is an enlarged detail derived from FIG. 8, one can see the central deflection which exists in the stopper, and that ports 24i are received well within the stopper's cup in the stopper in the vial, and closely adjacent the base of the cup.

Preferably, now, by up-ending this fully connected organization so that vial 30 is inverted, the plunger in the syringe is withdrawn, as indicated by the arrow in FIG. 8, to draw liquid diluent from the vial into the body of the syringe. The fact that ports 24i are well within the cup in the stopper, and closely adjacent the base of the cup, results in substantial assurance that essentially all of the liquid in the vial will be gathered.

Next, the now-emptied small vial is withdrawn by pulling it to the left away from the coupled syringe, as indicated in FIG. 10, with such withdrawal action automatically causing adaptor 26 to separate from device 24 and to remain attached to the smaller vial. Such convenient, automatic separation of adaptor 26 and device 24 is an advantageous feature of the apparatus of the invention.

Figures 11, 12, 13, 14:
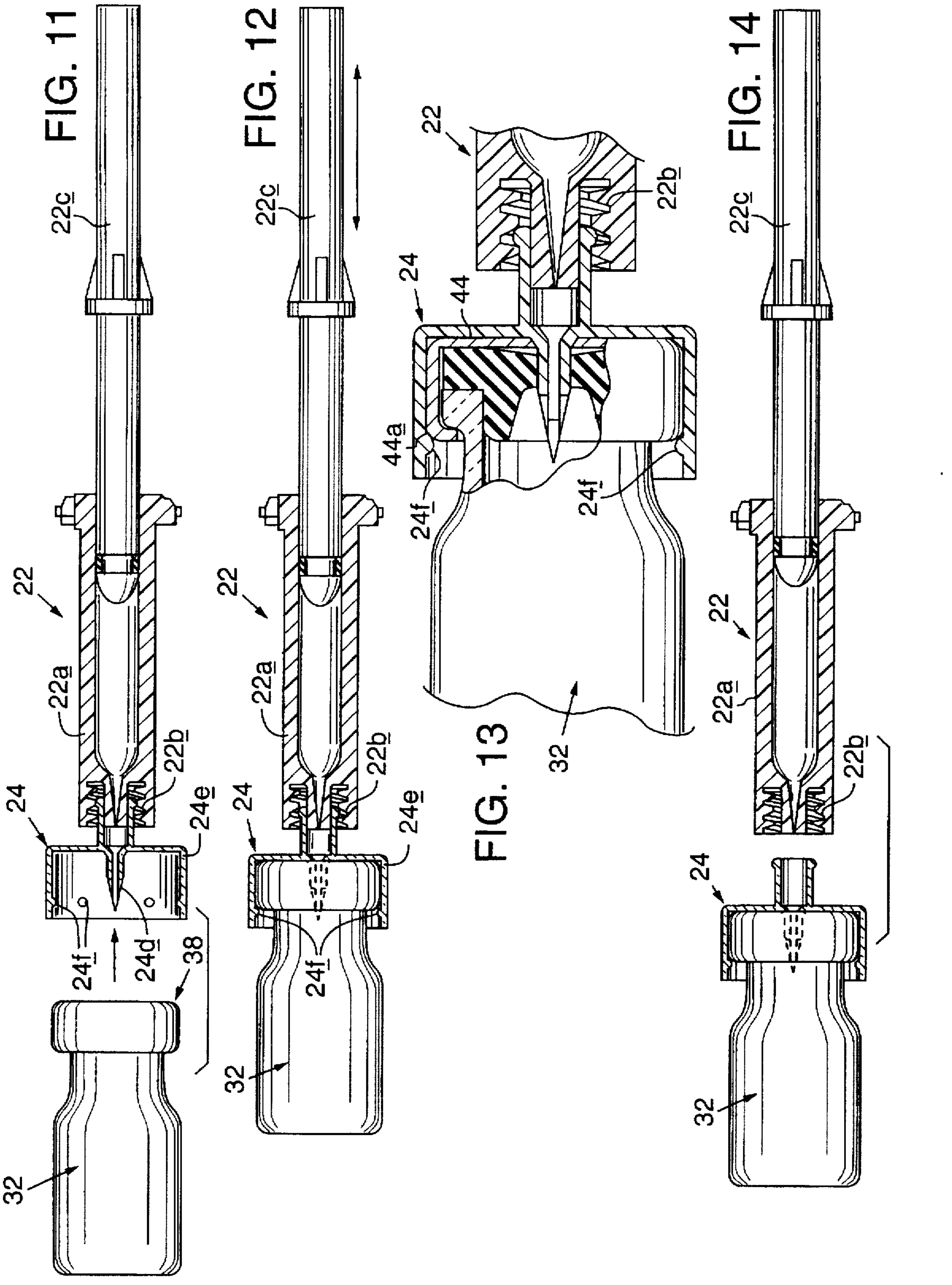

Next, and looking now at FIG. 11, the mouth end of a larger-size vial, such as vial 32, is directed as indicated toward vial-coupling end 24*b*, with the portion of shroud/collar 24*e* which extends longitudinally beyond spike 26*d* tending to gather, guide and centralize the mouth end of the vial relative to spike 24*d*. This action results in fall coupling of the larger vial with device 24, as indicated in FIG. 12. Under these circumstances, and now referring to FIG. 13, along with FIG. 12, one can see that the underside shoulder of the band in vial 32 is borne against and therefore gripped by protuberances 24*f*, and that ports 24*i* are positioned within the cup in the vial's stopper closely adjacent the base of that cup. Protuberances 24*f* tend to hold this larger vial in place against the same kind of involuntary ejection mentioned earlier—such ejection being promoted under the influence of central deflection in the stopper, which deflection is clearly evident in FIG. 13.

The plunger in the syringe is then moved as indicated by the double-ended arrow in FIG. 12, first inwardly into the body of the syringe to eject diluent liquid into vial 32 for the purpose of mixing and blending with the dry powdered medicine initially resident in vial 32, and after mixing, then outwardly from the body of the syringe to extract fully-blended pharmaceutical liquid.

With the construction of the apparatus of the invention as described, and considering the construction of the liquid-passage structure, liquid ejected into vial 32 exits ports 24*i* substantially radially against the adjacent surfaces of the stopper cup, and this action tends to cause liquid entering the vial to flow outwardly and downwardly along the inside wall of the vessel in the vial so as to minimize unwanted foaming. Ordinarily, this ejection activity takes place with the vial generally upright, or at least at some upwardly inclined angle. Withdrawing of blended material from vial 32 is typically accomplished by inverting the coupled assemblage so that substantially all of the blended material in the vial ultimately gathers near the base of the stopper's cup where it is readily accessible for extraction through into ports 24*i*.

With the syringe now filled with a fully-prepared dispensible liquid pharmaceutical, the syringe is decoupled from device 24 as indicated by FIG. 14.

In modern practice, the constituent elements of the apparatus of the invention are not re-used, and so remain with the now-spent vials with which they are discharged.

Reviewing very briefly an aspect of the procedure which has just been described, one should note that, because of the positional relationship which exists in each case where a vial is fully coupled for liquid transfer, the acting vial-grip structure is positioned relative to ports 24*i* in such a manner that the ports become properly positioned within the associated stopper cup.

Under circumstances where the apparatus of the invention is intended to be used in a single-size, two-vial procedure, only a device like liquid-transfer device 24 needs to be employed. The manner of practicing this procedure should be clear from the description which has just been given above, recognizing that decoupling of the first-used vial in the procedure is done without removing device 24 from the communication end of a coupled syringe.

Accordingly, the apparatus of the invention clearly meets the objectives and offers the advantages ascribed to it earlier herein. For example, it affords ready accommodation both of same-vial-sizes and of different-vial-sizes in a very easy manner. Foaming problems are greatly minimized, if not all together avoided. Gathering and withdrawing of liquid from a vial is facilitated by the close positioning which exists between the ports in the apparatus of the invention and the base of a cup in the stopper of a coupled vial.

While a preferred structural form of the invention has been described and illustrated herein, we appreciate that certain variations and modifications may be made without departing from the spirit of the invention.

We claim:

1. Liquid-transfer apparatus operatively interposable between a syringe and a vial, and accommodating sequential operative coupling first to the top of a vial having one size, and thereafter to the top of a vial having another, larger size, said apparatus comprising:

a liquid-transfer device including a syringe-coupling end, a vial-coupling end and liquid-passage structure effectively communicating between said ends, said vial-coupling end being sized for direct coupling to the top of a vial having such other, larger size, the liquid-transfer device further including vial-grip structure comprised of at least one radially-inwardly extending member located adjacent said vial-coupling end; and a vial-coupling adaptor removably receivable in a connected relationship with said vial-coupling end to adapt the same for coupling of the apparatus to the top of a vial having such smaller, one size;

said liquid-passage structure including an elongate channel extending axially from said syringe-coupling end toward said vial-coupling end, and at least one laterally facing port communicating with said channel adjacent said vial-coupling end, said liquid-passage structure, at the region of communication between said channel and said port, being constructed to limit liquid flow out of said port predominantly to generally radial flow relative to the long axis of said channel.

2. The apparatus of claim 1, wherein said port has an exit profile which has maximum transverse dimensions that lie in the range of about 0.02-to about 0.03-inches.

3. The apparatus of claim 2, wherein said exit profile has a cross-sectional area in the range of about 0.0004-in$^2$ to about 0.0009-in$^2$.

4. The apparatus of claim 1, wherein said vial-grip structure is disposed downstream from said port relative to said channel.

5. The apparatus of claim 1 wherein said adaptor includes vial-grip structure.

6. The apparatus of claim 5 in which, with the adaptor in a connected relationship with said vial-coupling end, said vial-grip structure is positioned downstream from said port relative to said channel.

7. The apparatus of claims 1, 4, 5, or 6 which is constructed for use with such different-sized vials each of the type including a vessel with a mouth closed by a pierceable stopper, and where each such stopper includes a hollow-interior, central annular, projecting wall structure with an open end defining a cup with a base facing (axially) the interior of the vessel, and wherein the positional relationship which exists between said port and said vial-grip structure, under circumstances with the device coupled to such a vial, is such that said port is located within the stopper's cup and closely adjacent the cup's base.

8. A method of transferring liquid between a syringe and a vial under circumstances that require accommodating sequential operative coupling first to the top of the vial having one size, and thereafter to the top of a vial having another larger size, said method comprising:

utilizing liquid-transfer apparatus which includes a liquid-transfer device including a syringe-coupling end, a vial-coupling end sized to receive directly the top of a vial having such other, larger size, and liquid-passage structure communicating between these ends, and a vial-coupling adaptor removably receivable in a connected relationship with the mentioned vial-coupling end to adapt the same for coupling of the apparatus to the top of a vial having such smaller, one size;

establishing a connected relationship between the liquid-transfer device and the vial-coupling adaptor;

coupling a selected syringe and a selected vial having such smaller, one size;

performing a liquid-transfer operation between the selected syringe and the selected vial;

decoupling the first selected vial, and by said decoupling automatically disconnecting the vial-coupling adaptor and the liquid-transfer device;

selecting a second vial of the type characterized by such other, larger size and coupling the same to the vial-coupling end in the liquid-transfer device; and performing at least one other liquid-transfer operation.

9. Liquid-transfer apparatus operatively interposable between a syringe and a vial, and accommodating sequential coupling first to the top of a vial having one size, and thereafter to the top of a vial having another, larger size, said apparatus comprising:

a liquid-transfer device including a syringe-coupling end, a vial-coupling end and liquid-passage structure communicating between the ends, the vial-coupling end being sized for direct coupling to the top of the vial having such other, larger size; and a vial-coupling adaptor removably mounted to the vial-coupling end to adapt the same for coupling of the apparatus to the top of a vial having such smaller, one size;

the liquid-passage structure including an elongate channel extending from the syringe-coupling end toward the vial-coupling end, and at least one laterally facing port communicating with the channel adjacent the vial-coupling end.

10. Liquid-transfer apparatus operatively interposable between a syringe and a vial, and accommodating sequential coupling first to the top of a vial having one size, and thereafter to the top of a vial having another, larger size, said apparatus comprising:

a liquid-transfer device including a syringe-coupling end, a vial-coupling end and liquid-passage structure communicating between the ends, the vial-coupling end being sized for direct coupling to the top of the vial having such other, larger size, the vial-coupling end including at least one radially-inwardly extending member disposed adjacent the vial-coupling end for removably engaging the vial; and a vial-coupling adaptor removably receivable in the vial-coupling end to adapt the same for coupling of the apparatus to the top of a vial having such smaller, one size;

the liquid-passage structure including an elongate channel extending from the syringe-coupling end toward the vial-coupling end, and at least one laterally facing port communicating with the channel adjacent the vial-coupling end.

* * * * *